(12) United States Patent
Skelton et al.

(10) Patent No.: US 11,857,705 B2
(45) Date of Patent: Jan. 2, 2024

(54) METHOD OF TREATING A SPACE

(71) Applicant: PetAirapy LLC, St. Charles, IL (US)

(72) Inventors: David Skelton, Bartlett, TN (US);
Mike M. Uda, St. Charles, IL (US)

(73) Assignee: AERAPY LLC, St. Charles, IL (US)

( * ) Notice: Subject to any disclaimer, the term of this patent is extended or adjusted under 35 U.S.C. 154(b) by 596 days.

(21) Appl. No.: 16/876,548

(22) Filed: May 18, 2020

(65) Prior Publication Data

US 2020/0324012 A1 Oct. 15, 2020

Related U.S. Application Data

(63) Continuation-in-part of application No. 16/854,128, filed on Apr. 21, 2020, now abandoned, which is a continuation-in-part of application No. 15/871,719, filed on Jan. 15, 2018, now Pat. No. 10,753,626.

(51) Int. Cl.
*A61L 9/20* (2006.01)
*G01P 13/00* (2006.01)

(52) U.S. Cl.
CPC .............. *A61L 9/20* (2013.01); *G01P 13/00* (2013.01); *A61L 2209/12* (2013.01)

(58) Field of Classification Search
CPC ................................ A61L 9/20; A61L 2209/12
See application file for complete search history.

(56) References Cited

U.S. PATENT DOCUMENTS 6,908,597 B2 6/2005 Chen
10,363,329 B2 7/2019 Childress
2004/0146437 A1 7/2004 Arts et al.
2009/0117000 A1* 5/2009 First .......................... A61L 9/20
 422/24
2010/0003165 A1* 1/2010 McEllen ................ H05B 41/39
 422/4

(Continued)

FOREIGN PATENT DOCUMENTS

GB 2515842 A * 1/2015 ............ A61L 9/122
JP 6607623 B1 11/2019

OTHER PUBLICATIONS

Request for Ex Parte Reexamination No. 90/014,918, filed Dec. 7, 2021, of U.S. Pat. No. 10,753,626.

(Continued)

*Primary Examiner* — Kevin Joyner
(74) *Attorney, Agent, or Firm* — Wood, Phillips, Katz, Clark & Mortimer

(57) ABSTRACT

An air treatment unit having a frame and a source of UV light, with the frame having an air guidance assembly. Air within a primary treatment volume is guided by the frame to move radially outwardly from the primary treatment volume through a dispersion angle. Air within the primary treatment volume is exposed to UV light rays from the UV light source. The air treatment unit is changeable between: a) a first state wherein a predetermined part of a volume of space within which the air treatment unit resides is strategically blocked from direct exposure to UV light rays generated by the UV light source; and b) a second state wherein at least a portion of the predetermined part of the volume of space is directly exposed to UV light rays from the UV light source.

25 Claims, 11 Drawing Sheets

(56) References Cited

U.S. PATENT DOCUMENTS

| | | | |
|---|---|---|---|
| 2013/0291735 A1* | 11/2013 | Livchak | F24F 1/0047 165/48.1 |
| 2014/0060094 A1 | 3/2014 | Shur et al. | |
| 2014/0067130 A1* | 3/2014 | Pillai | B60H 3/0007 315/297 |
| 2015/0086420 A1* | 3/2015 | Trapani | A61L 9/20 422/24 |
| 2016/0220716 A1 | 8/2016 | Childress et al. | |
| 2016/0271289 A1 | 9/2016 | Duffy | |
| 2017/0321877 A1 | 11/2017 | Polidoro | |
| 2019/0060496 A1 | 2/2019 | Tillotson | |
| 2019/0091738 A1 | 3/2019 | Chen | |
| 2020/0254125 A1 | 8/2020 | Lloyd | |

OTHER PUBLICATIONS

International Search Report dated Mar. 15, 2021 in International Patent Application No. PCT/US2020/066579.

* cited by examiner

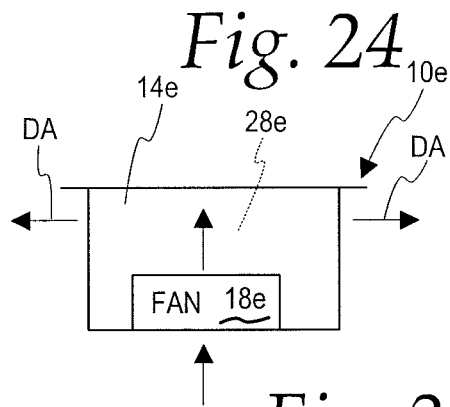
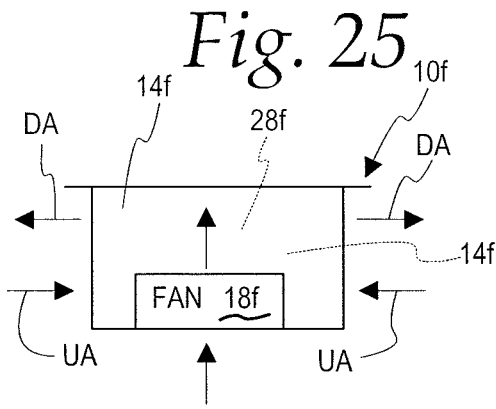
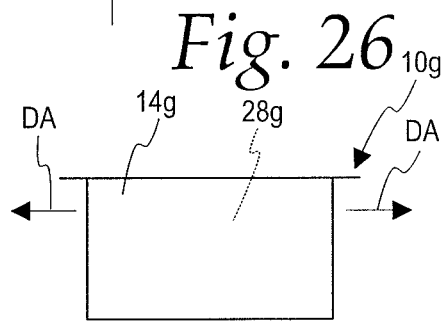
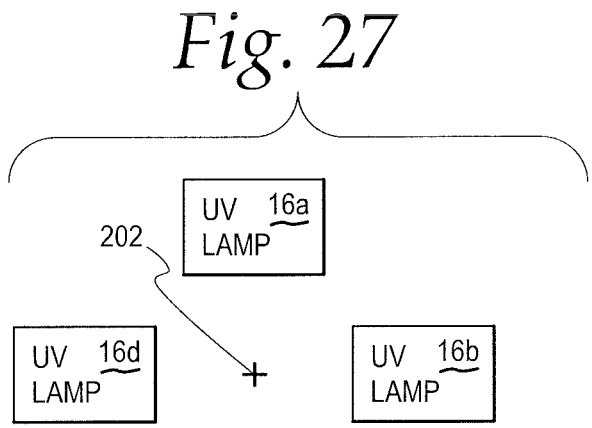
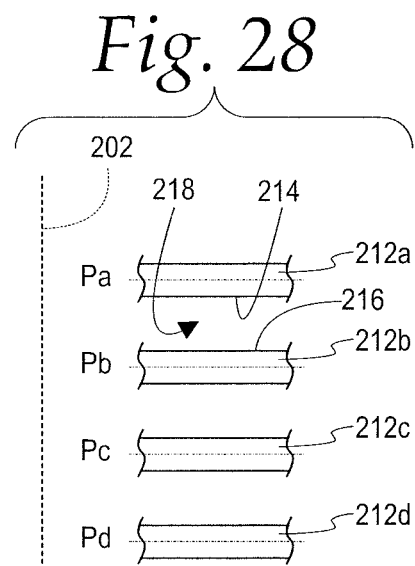
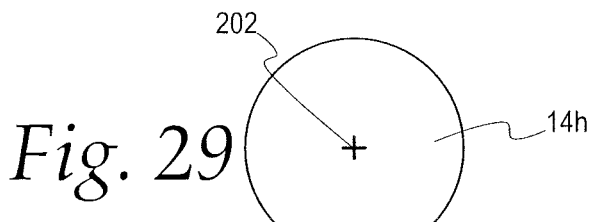
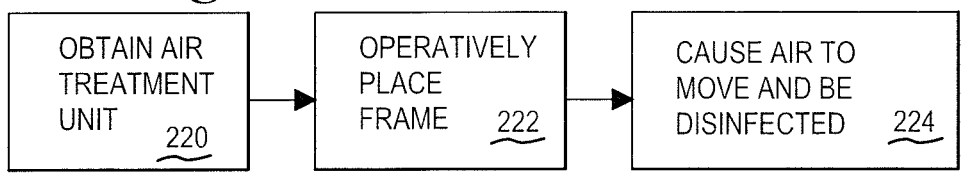

METHOD OF TREATING A SPACE

CROSS-REFERENCE TO RELATED APPLICATIONS

This application is a continuation-in-part of U.S. patent application Ser. No. 16/854,128, filed Apr. 21, 2020, which is a continuation-in-part of U.S. patent application Ser. No. 15/871,719, filed Jan. 15, 2018.

BACKGROUND OF THE INVENTION

Field of the Invention

This invention relates to environmental air treatment and, more particularly, to a treatment unit that causes air to be disinfected by being exposed to UV light.

Background Art

UV-C, also known as "germicidal ultraviolet" light, is known to deactivate molds, spores, and germs contained in tiny airborne droplet nuclei that transmit diseases such as measles, tuberculosis, and influenza from animal or human to animal or human. With significant intensity, UV-C can penetrate the cell wall of a microorganism and destroy it, but cannot penetrate the outer layer of a pet's or a human's skin or the cornea of the eye.

A multitude of systems have been devised to treat environmental air in which humans and pets reside. UV-C fixtures are currently available for disinfecting air as it is mechanically forced through ventilation ductwork and proximate to germicidal lamps, commonly referenced as "in-duct" UV-C fixtures. The radiation from the UV-C fixture neutralizes pathogens that would otherwise contaminate air as they are mixed and circulated/recirculated via one or more ventilation air ducts. A system fan moves contaminated air through ductwork, as an incident of which airborne pathogens are forced to pass proximate to and through a germicidal energy field generated by one or more UV-C lamps located in the air path/supply vent.

Specific pathogens can be targeted by applying published lethal UV-C energy doses to the air as it passes through the ductwork and the supply vent that distributes air to a space. These in-duct UV-C fixtures are commonly mounted in one of three locations: a) within the ductwork; b) in the air plenum proximate to HVAC cooling/heating coils; and/or c) at or inside the supply vent as the air exits the duct and is dispersed through a space.

In-duct air disinfection is achieved when air is mechanically forced through a ventilation system, past one or more UV-C lamps, and into a space through a supply vent.

Another form of system uses UV-C fixtures to disinfect air that naturally or mechanically rises upwardly within a room at a height above occupants' heads. These fixtures are commonly mounted to upper walls or ceilings and project germicidal light outwardly in a generally horizontal path. This "upper-air" disinfection technology exploits the natural, passive movement of air within a space through the physical law of convection—hot air rising and cool air falling.

Any source of heat in a space accelerates convection rates. Upper-air fixtures employ UV-C lamps to generate light energy that is broadcast into a room at a specific height, typically at seven feet or more to be overhead standing room occupants. Light baffles or louvers cause the germicidal energy to be dispersed into the space in a tightly defined, narrow, energy band, known as an airborne pathogen "kill zone" of UV-C light energy.

In spaces with taller ceilings—typically 9+ feet—open fixtures can flood the upper part of the room while a shelf or lip prevent germicidal light from dispersing into the lower, occupied space in the room. These upper-air fixtures are often referenced as TB, or tuberculosis, lights, given their common use in countries with high occurrences of tuberculosis and other respiratory diseases. Fans may be used to accelerate and assist in increased air turn rates to increase the movement of contaminated air through the germicidal energy zone. Air disinfection is achieved only when air is moved, either mechanically or naturally, through the germicidal disinfection field created in the upper room space.

It is also known to disinfect air by forcing air through dedicated, defined disinfection chambers. These systems may be wall-mounted, hung from ceilings, or installed in conjunction with another type of system. This category of system pushes or pulls contaminated air through a fixed chamber, proximate to a UV-C germicidal lamp, and then causes the treated air to be distributed into a space. These systems are similar in structure and operate on the same basic principles as conventional floor air cleaners. Air disinfection is achieved only when air is mechanically pulled or pushed through the enclosed system, past a UV-C lamp, and then forced into a space.

Air destratification is practiced to be complementary to one or more of the above systems. Because cool air falls and warm air rises, stagnant air becomes stratified in confined spaces with warm air accumulating near the ceiling and cold air near the floor. Destratification technology uses one or more fans to accelerate the natural convection movement of contaminated air through a UV-C "kill zone". If there is little or no heat source to generate sufficient convection currents, and no mechanical movement of stagnant air in a room, one or more fans may be used to move warm air from near the upper part of a room toward the floor, and conversely move cool air near the floor to the upper part of a room. The objective of the destratification is to eliminate hot/cold spots and create an environmental average of hot/cold air temperatures and to move air through the UV-C "kill zone". Existing paddle-type ceiling fans are commonly used for purposes of destratification and air mixing to improve the efficiency of air disinfection technology.

Air treatment systems using UV light typically are constructed to be dedicated to either: a) surface treatment; b) or circulating air treatment within a space. In the former case, surfaces to be sanitized are directly exposed to the light rays from the UV light source. Since exposure to UV light rays can be dangerous to human beings and animals, these systems are designed to be operated in either small enclosures or in larger rooms only when unoccupied by humans or animals.

Typically, the latter category of systems is constructed and operatively positioned so that air within a space can be continuously treated and circulated while the space is occupied. The system and space geometries are such that the occupants, moving normally within the entire space, are shielded from direct exposure to light rays from the UV light source.

While both categories of system are effective for their intended purposes, users heretofore have generally been required to either: a) select one or the other of the systems based upon whether surface treatment or circulating air treatment is a priority; or b) obtain both types of systems and operate those in the dedicated surface treatment category only when no humans or animals are present and potentially within the path of emanating rays from the UV light source. The former option limits the type of treatment whereas the latter may require a significant outlay to purchase separate systems that may not be easily incorporated into the same space and which may require a coordinated use that may be difficult and/or inconvenient to carry out.

A surface treating system that has the capacity to flood an entire room may create additional challenges in terms of basic operation. That is, protective gear may have to be worn to allow an operator to turn the system on and thereafter exit the space without dangerous exposure to the UV light rays.

The industry continues to seek improved systems that will more effectively deactivate molds, spores, and germs in spaces occupied by humans and pets, without causing user inconvenience or presenting any health hazard to humans, pets, or other animals.

SUMMARY OF THE INVENTION

In one form, the invention is directed to a method of treating a space. The method includes the steps of: obtaining an air treatment unit having a frame and a source of UV light; and changing the air treatment between: a) a first state, wherein a predetermined part of a volume of space outside of the air treatment unit and within which the air treatment unit resides is strategically blocked from direct exposure to UV light rays generated by the UV light source; and b) a second state, wherein at least a portion of the predetermined part of the volume of space is directly exposed to UV light rays from the UV light source. The frame is configured to define a primary treatment volume with an axis. The frame further includes an air guidance assembly. The air treatment unit is configured so that air within the primary treatment volume is guided by the frame to move radially outwardly from the primary treatment volume through a dispersion angle. Air within the primary treatment volume is exposed to UV light rays from the UV light source so that air that moves radially outwardly from the primary treatment volume is disinfected. The air treatment unit has a top and a bottom spaced axially from the top. With the air treatment unit in the second state, at least part of the at least portion of the predetermined part of the volume of space that is directly exposed to UV light rays from the UV light source is below the air treatment unit.

In one form, the dispersion angle is at least 90°.

In one form, the air treatment unit has a top and a bottom spaced axially from the top. With the air treatment unit in the first state, at least a portion of the predetermined part of the volume is directly below the air treatment unit.

In one form, the frame has a wall with at least one opening with a first effective area through which UV light rays from the source of UV light are directed with the treatment unit in the second state.

In one form, with the treatment unit in the first state, the at least one opening has an effective area less than the first area.

In one form, the wall is a bottom wall and with the treatment unit in the first state, the at least one opening is substantially fully blocked.

In one form, the air treatment unit further includes an air moving assembly which induces movement of air radially outwardly from the primary treatment volume.

In one form, the air treatment unit has an air moving assembly which induces movement of air from within a space in which the air treatment unit resides into the primary treatment volume.

In one form, the air moving assembly is maintained on the frame.

In one form, the air guidance assembly guides air within the primary treatment volume in movement radially outwardly from the primary treatment volume.

In one form, the air guidance assembly is configured to define at least one elongate opening through which air within the primary treatment volume is communicated in moving radially outwardly from the treatment volume.

In one form, the air guidance assembly has a plurality of spaced slats. The at least one elongate opening has a louver volume between at least first and second of the spaced slats.

In one form, the first and second spaced slats are in radially overlapping relationship.

In one form, the air treatment unit is configured to create multiple zones in which air is treated differently by UV light rays from the UV light source. The multiple zones include: a) a first zone in the primary treatment volume; and b) a second zone in the louver volume.

In one form, the UV light source is a UV lamp residing one of: a) within; and b) adjacent to, the primary treatment volume.

In one form, the multiple zones further include a third zone that is radially outside of the first and second slats.

In one form, the first and second slats are substantially flat and reside in first and second planes that are substantially orthogonal to the axis of the primary treatment volume.

In one form, the air treatment unit has on and off states. A delayed start timer can be set to at least one of: a) cause the treatment unit to change from the off state into the on state; and b) cause the treatment unit to change between the first and second states, after a predetermined time interval.

In one form, the treatment unit has at least one blocking part that is repositionable to change the treatment unit between the first and second states.

In one form, the treatment unit has a timer that can be operated to cause the treatment unit to be one of: a) maintained in the on state; and b) operated in the second state, for a predetermined time interval.

In one form, the treatment unit has an on state and an off state. The treatment unit further includes a disabling feature that causes the treatment unit to be changed from one of: a) the on state into the off state; and b) the second state into the first state upon a predetermined triggering event occurring at a location spaced from the treatment unit.

In one form, the air treatment unit is provided in combination with a structure having a space within which the treatment unit is operatively placed. The treatment unit further includes a motion sensor. The predetermined triggering event is movement of an object in the vicinity of the motion sensor.

In one form, the structure has an entry door to the space within which the treatment unit is operatively placed and which is movable between open and closed positions. The treatment unit has a disabling switch. The predetermined triggering event is movement of the entry door from the closed position into the open position. The disabling switch causes the unit to be changed from one of: a) the on state into the off state; and b) the second state into the first state.

BRIEF DESCRIPTION OF THE DRAWINGS

FIGS. 20-26 are schematic representations showing different contemplated configurations for the inventive air treatment unit in terms of how untreated air is delivered to the primary treatment volume and disinfected air is discharged from the air treatment unit;

FIG. 27 is a schematic representation of one layout of UV lamps on the inventive air treatment unit;

FIG. 28 is an enlarged, fragmentary, elevation view of a plurality of slats making up part of a frame on the inventive air treatment unit;

FIG. 29 is a schematic depiction showing a perimeter shape of a frame on the inventive air treatment unit taken along the axis of the primary treatment volume thereon;

FIG. 30 is a flow diagram representation of a method of treating air in a space, according to the invention;

DETAILED DESCRIPTION OF THE PREFERRED EMBODIMENT

Figure 1:
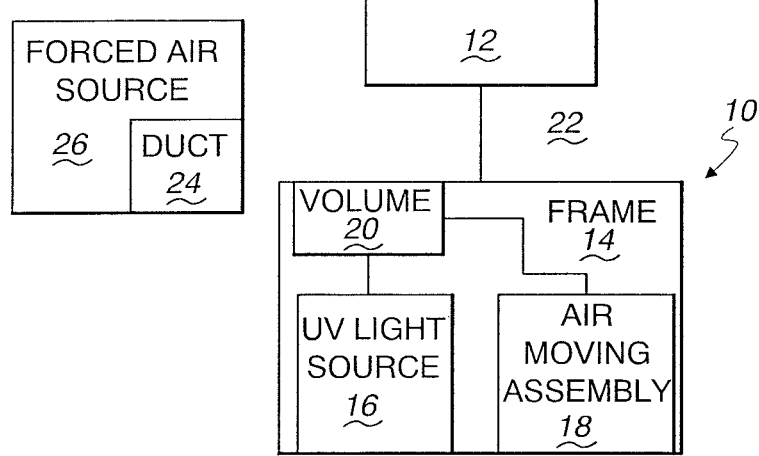
FIG. 1 is a schematic representation of one form of air treatment unit, according to the invention.

In FIG. 1, an air treatment unit, according to the present invention, is shown in schematic form at 10. The air treatment unit 10 is preferably configured to be attached to a wall 12, which is most preferably a ceiling wall, but could be a peripheral side wall surrounding an occupiable space.

The air treatment system 10 has a frame 14 that is mounted to the wall 12. The frame 14 supports a light source 16, characterized herein as a "UV light source", which is intended to encompass all different forms of light known to those skilled in the art capable of deactivating molds, spores, germs, etc., that are entrained in air, to thereby effect disinfecting of that air.

The frame 14 further supports an air moving assembly 18 that causes air within a space to be directed into a frame volume 20 that has UV rays from the source 16 therein capable of disinfecting air.

By mounting the frame 14 to the wall 12, the frame 14 and UV light source 16 are maintained in an operative position within a space 22 in which air is to be disinfected. The air moving assembly 18 causes room air to be directed into the volume 20, wherein it is treated by the UV light source and thereafter reintroduced to the space 22.

The frame 14 is also configured to allow air expelled from a duct 24 on a forced air source 26 to be directed into the volume 20 for treatment by the UV rays from the light source 16.

Figure 2:
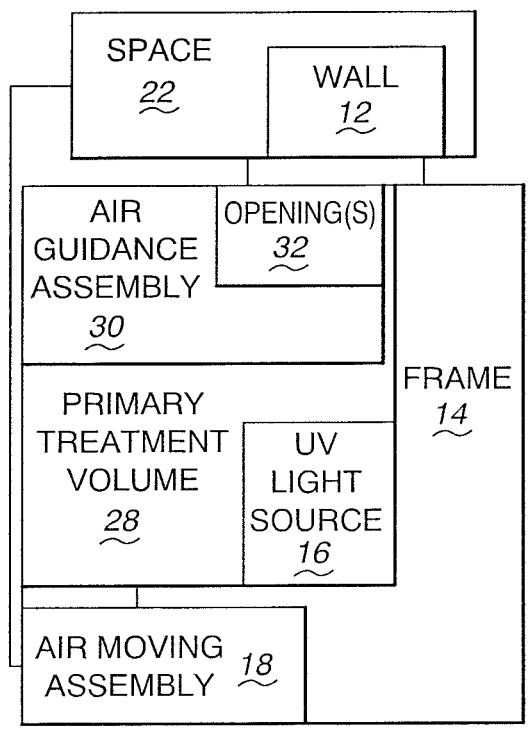
FIG. 2 is a schematic representation of a more specific form of air treatment unit as in FIG. 1.
Figure 3:
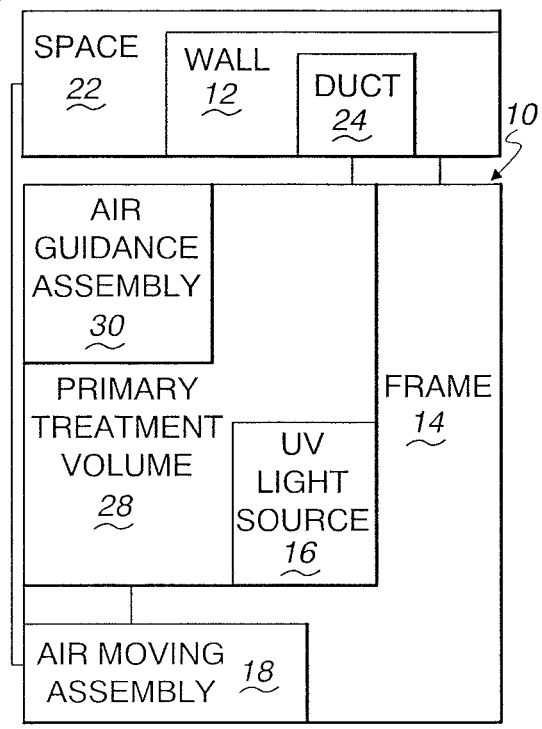
FIG. 3 is a schematic representation of an alternative form of air treatment unit as shown generically in FIG. 1.

FIGS. 2 and 3 show alternative setups for the air treatment unit 10 within the space 22. In these Figures, additional details of the air treatment unit 10 are also shown.

In FIG. 2, a primary treatment volume 28 is shown on the frame 14 with direct exposure to the operatively positioned UV light source 16. In the primary treatment volume 28 there is an active germicidal energy field. An air guidance assembly 30 has at least one opening 32, preferably with an elongate configuration, through which air from the primary treatment volume 28 passes to be distributed to the space 22 with the frame 14 operatively positioned on the wall 12. Preferably, the opening(s) 32 has/have a louver arrangement wherein UV light from the source 16 creates a kill zone within the volume of the openings 32 wherein the air is further disinfected before dispersing into the space 22.

Immediately outside of the frame 14 there exists a passive external germicidal energy field that treats the room air. That is, UV rays are directed through the louver volumes/openings 32 to the region immediately outside of the frame 14 and have sufficient intensity in this region to effect a significant level of passive treatment.

The air moving assembly 18 forces air from the space 22 into the primary treatment volume 28 to avoid room air stagnation.

The system 10 in FIG. 3 has the same basic construction for the frame 14, and similar components thereon, including the UV light source 16, the primary treatment volume 28, the air guidance assembly 30, and the air moving assembly 18.

Additionally, the frame 14 is configured so that the aforementioned duct 24 on the wall 12 forces air, typically conditioned through an HVAC system, directly into the primary treatment volume 28.

When the forced air source 26 and air moving assembly 18 are operating at the same time, air from the duct 24 and air moving assembly 18 is caused to mix within the primary treatment volume 28, wherein it is treated by the UV radiation from the source 16.

The schematic representation of components in FIGS. 1-3 is intended to encompass the components, as shown in specific embodiments described hereinbelow, and virtually an unlimited number of variations of those components and their interaction. The preferred embodiments described herein are exemplary in nature only and represent specific forms of the invention as generically defined in FIGS. 1-3.

Figure 4:
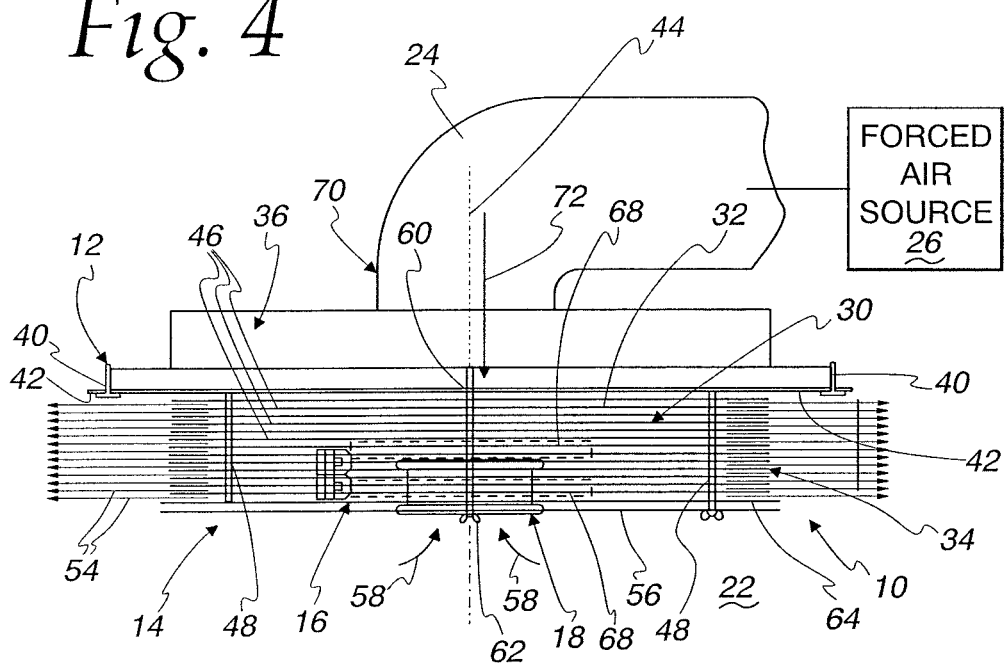
FIG. 4 is a side elevation view of one specific form of the inventive air treatment unit, as shown generically in FIG. 1, and in an operative state with respect to an existing duct which introduces treated air into a space.
Figure 5:
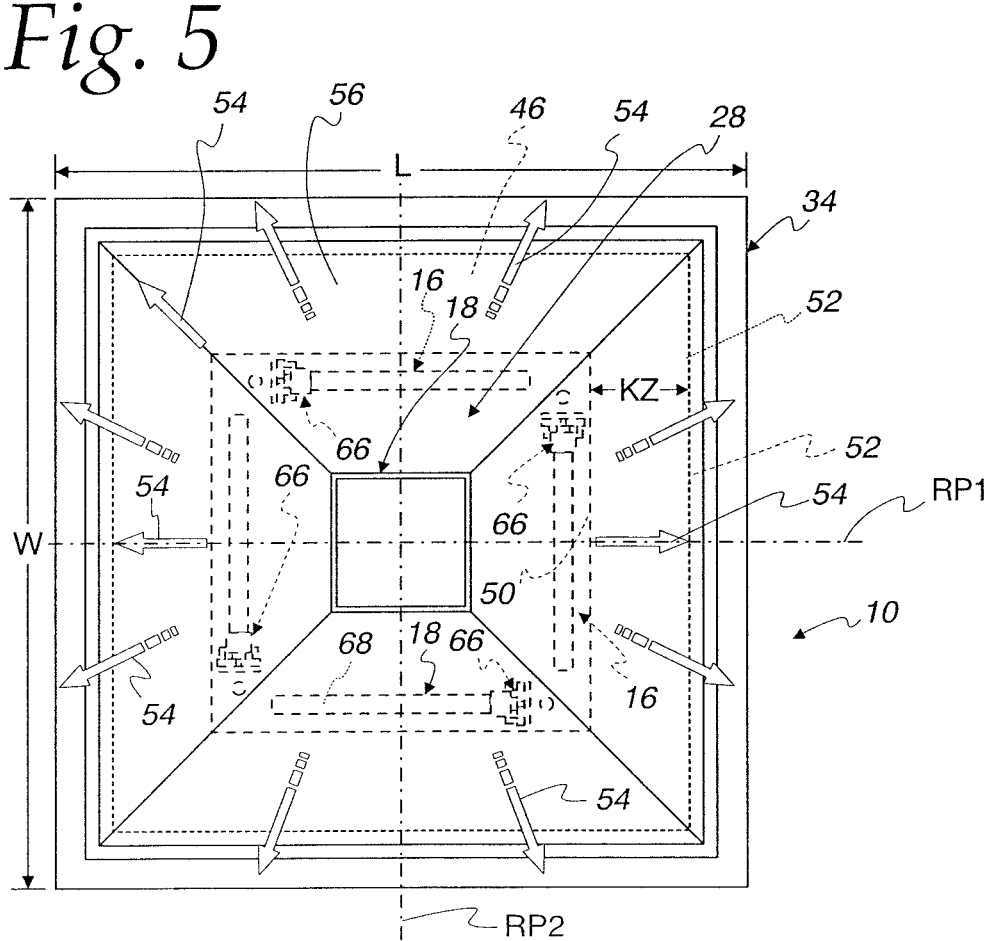
FIG. 5 is a bottom view of the air treatment unit in FIG. 4.

One exemplary form of the air treatment unit 10 is shown in FIGS. 4 and 5. The frame 14 has a main frame portion 34 and a subframe portion 36.

The subframe portion 34 is used to effect mounting of the frame 14 to the wall 12. In this embodiment, the subframe portion 36 has a mounting portion 38 that spans between, and is supported upon, T-bar components 40 on a ceiling grid T-bar system so that with the frame 14 in the operative position of FIG. 4, the main frame portion 34 depends from the downwardly facing ceiling surface 42.

In this embodiment, the length L and width W of the frame 14 are the same, with one preferred length and width dimension being 24 inches. Making the length L and width W the same is not a requirement, nor is a squared shape. Room geometry may dictate a different optimal shape.

The components in FIGS. 4 and 5 are shown substantially to scale based upon the length and width L, W each being twenty four inches. The primary treatment volume 28 has a square shape as viewed along a vertical central axis 44. The air guidance assembly 30 extends around and effectively frames the primary treatment volume 28, as viewed from below in FIG. 5.

The air guidance assembly 30 consists of a series of slats 46, each with a square frame shape. The slats 46 are mounted through a plurality of rods 48 depending from the subframe portion 36. The slats 46 are flat, radially overlap, and are mounted in a close vertically spaced relationship to define louver volumes corresponding to the aforementioned elongate opening(s) 32. The louvers/openings 32 define the aforementioned kill zone as air distributes radially outwardly relative the central axis 44 from the primary treatment volume 28 and funnels into the volume between the inner edges 50 of the slats 46 and the perimeter outer edges 52 thereof. This kill zone region is identified by the width dimension KZ in FIG. 5. Air is forced to travel controllably in a confined path and in a radial direction through the volume of the louvers/openings 32 over the distance KZ and, in its overall path within the treatment energy field, between the primary treatment volume 28 and a region of the space 22 outside of the primary treatment volume.

With this arrangement, air within the primary treatment volume 28 distributes through the louvers/openings 32 radially in a pattern substantially 360° around the central axis 44. This flow pattern is identified generally by the arrows 54.

Air flow into the primary treatment volume 28 in a downward direction is blocked by a bottom wall 56 on the frame 14, which defines the lower boundary of the primary treatment volume 28.

The bottom wall 56 supports the air moving assembly 18, which is a conventional-type fan that draws air from the space 22 generally axially upwardly into the primary treatment volume 28, as indicated by the arrows 58.

The bottom wall 56 and air moving assembly 18 can be constructed to move as one piece and are supported together on hanging rods 60 depending from the subframe portion 36. A wingnut 62 is shown for securing the bottom wall 56 on the bottom of one of the hanger rods 60 in the operative position of FIG. 4, wherein the bottom wall 56 blocks the primary treatment volume 28 and provides a decorative cover for the unit 10, including over the downwardly facing surface 64 of the bottommost slat 46. With this arrangement, by removing the wingnuts 62, the bottom wall 56 and air moving assembly 18 thereon can be lowered to better access the air moving assembly 18 and to also access the primary treatment volume 28 and the plurality of lamps 66, together making up the UV light source 16.

In this embodiment, four lamps 66 are mounted to the frame 14 at equal distances from the central axis 44. The lamps 66 are arranged at regular angular intervals around the axis 44. In this embodiment, the lamps 66 cooperatively produce a square shape that is complementary to the shape of the primary treatment volume 28. As viewed along the axis 44, four radial lines spaced at 90° to each other are capable of passing, one each, through a different lamp 66. As depicted, each lamp 66 includes a pair of bulbs 68. Precise construction of the lamps 66 and their placement may vary considerably. One skilled in the art could readily come up with different arrangements to maximize exposure of air to the UV radiation generated by the lamps 66 within the primary treatment volume 28, the kill zone region in the louvers/openings 32, as well as in the passive treatment region outside of the frame 14.

The ability to separate the bottom wall 56 facilitates placement and maintenance of the lamps 66, as to change bulbs 68, and also permits cleaning of the slats 46 which may accumulate dust over time which contrasts with the preferred black coloration of the exposed slat surfaces.

The subframe portion 36 is constructed so that the duct 24 can be connected thereto or positioned in relationship therewith, so that a discharge region 70 expels air from the forced air source 26 preferably downwardly, as indicated by the arrow 72, directly into the primary treatment volume 28. The forced air source 26 may be any type of structure that produces pressurized air and is typically one that delivers heated or cooled air under pressure to and through the duct 24 into the space 22.

While not required, in the depicted embodiment, the central axis 44 coincides with the downwardly moving path of air from the duct 24 and the upwardly moving path of air generated by the air moving assembly/fan 18. As depicted, the axis 44 is at the center of both paths, which are substantially parallel to each other.

The upwardly and downwardly directed air paths at least partially coincide so that air in the separate paths is caused to mix within the primary treatment volume 28 and is thereafter diverted in a non-vertical direction through the louvers/openings 32 into a region of the space outside of the primary treatment volume 28.

Commonly, the air moving assembly 18 will be running constantly with the air treatment unit 10 in an "on" state. Thus, air is continuously drawn from the space 22 upwardly into the primary treatment volume 28, exposed to the radiation field generated by the UV light source 16 therein, and further treated in the kill zone within the louvers/openings 32 from where it is dispersed back into the space 22, and there passively treated in a region immediately outside of the frame 14.

When the forced air source 26 is operated, the incoming flow of air from the duct 24 becomes exposed to the radiation within the primary treatment volume 28 as it is mixed with the flow generated by the air moving assembly/fan 18. Thus, the incoming air is disinfected by the air treatment unit 10 as it is introduced into the space 22. The pressure from the duct air causes a higher pressure distribution of air radially outwardly from the air treatment unit 10 relative to the axis 44.

It should be understood that the invention also contemplates a more passive introduction of duct air as contemplated in the FIG. 2 embodiment.

Further, the description of the structure in FIGS. 4 and 5, and others hereinbelow, relative to a ceiling mount is intended to be exemplary as one particular operative position for the air treatment unit 10. The air treatment unit 10 could be mounted other than on a ceiling. Thus, the reference to vertical and horizontal should not be limited to a ceiling mount, and these references are arbitrary in the event that the air treatment unit is mounted in another orientation. For example, by changing the orientation of the air treatment unit 10, the basic principles of operation are similar, even if not preferred. While the axis orientation may be changed to an extent to become horizontal, for purposes of simplicity in the claims and description herein, "vertical", in characterizing the axis orientation, is an arbitrary reference that is not limited to any specific orientation.

Also, while not necessary, for purposes of uniformity of air treatment, the frame 24 is symmetrical on diametrically opposite sides of a reference plane containing the vertically extending axis 44. In this embodiment, the frame is symmetrical about orthogonal reference planes RP1, RP2 extending through the central axis 44.

Some variations in the air treatment unit 10, as described above, will now be described. Again, it is should be emphasized that these different versions are intended only to be exemplary in nature, showing other potential operating features and mounting options.

Figure 6:
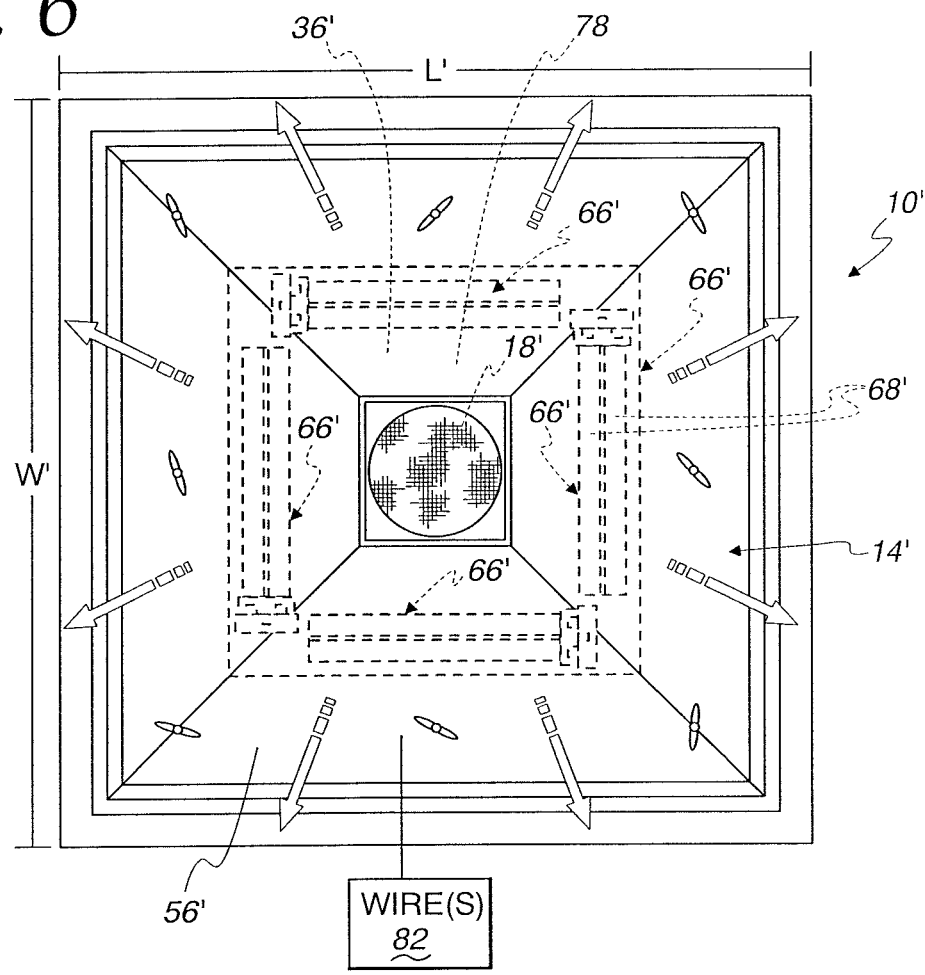
FIG. 6 is a view as in FIG. 5 of a modified form of air treatment unit, according to the invention.
Figure 7:
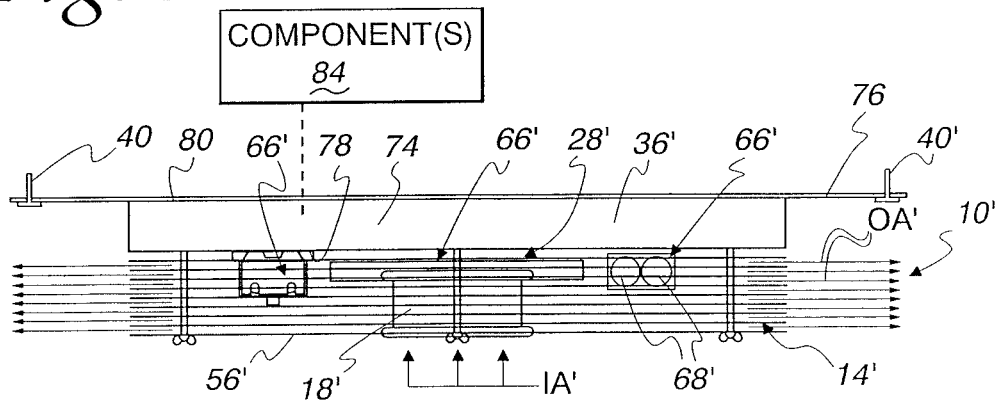
FIG. 7 is a side elevation view of the air treatment unit in FIG. 6.

In FIGS. 6 and 7, a treatment unit 10' is shown that is similar to the treatment unit 10 with a primary difference being that the subframe portion 36' is modified from the subframe 36. In this embodiment, the subframe portion 36' has a squared housing 74 with an upper, outwardly projecting flange 76 that is supported on T-bar components 40 on a drop ceiling to maintain the frame 14' in its operative position.

The lamps 66' are mounted on a downwardly facing surface 78 on the housing 74 within a primary treatment volume 28'. The lamps 66' are arranged so that the bulbs 68' are in side-by-side relationship as opposed to in vertically spaced relationship, as shown for the bulbs 68 in FIGS. 4 and 5.

An air moving assembly/fan 18' is mounted on a bottom wall 56' to draw in room air in a direction of the arrows IA', with treated air directed into the room space in a pattern indicated by the arrows OA'.

The air treatment unit 10' otherwise generally functions in the same manner as the air treatment unit 10, as described above.

The top wall 80 of the subframe portion 36' may have an opening as large as a discharge opening on the duct 24, or may simply allow passage of one or more wires 82 associated with electrical components 84 on the frame 14' and required to operate the lamps 66', air moving assembly/fan 18', and any other electrical components.

Figure 8:
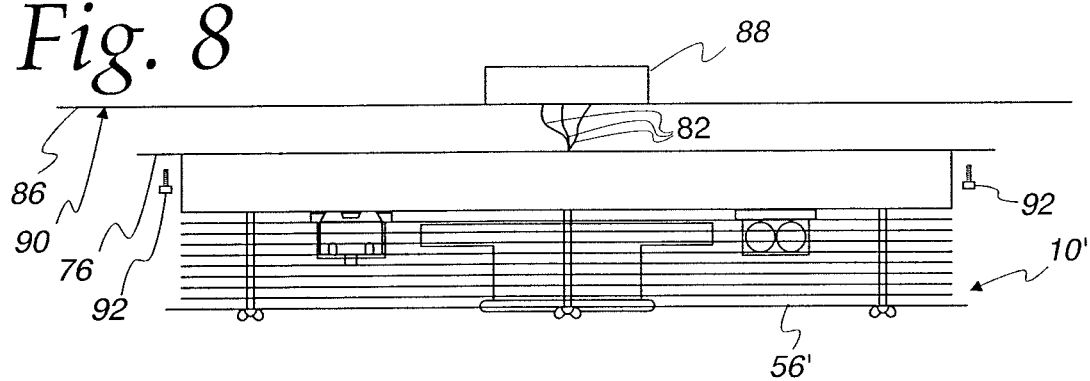
FIG. 8 is a side elevation view as in FIG. 7 with the air treatment unit lowered with respect to a mounting wall.
Figure 9:
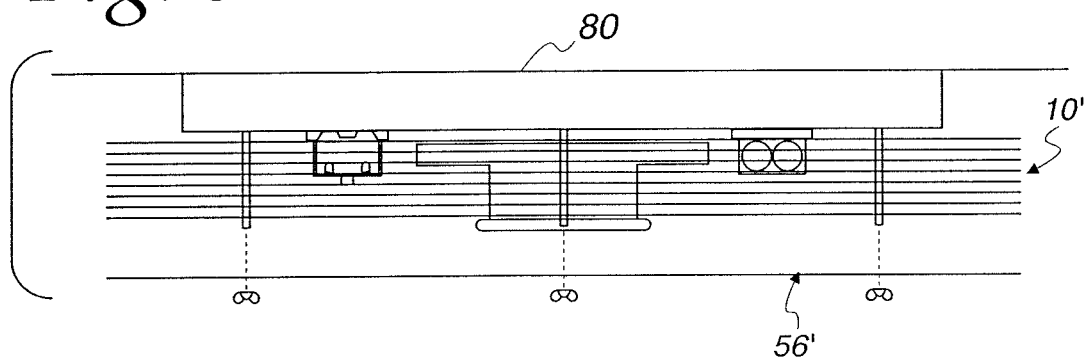
FIG. 9 is a view as in FIG. 8 with a bottom wall on the air treatment unit separated.
Figure 10:
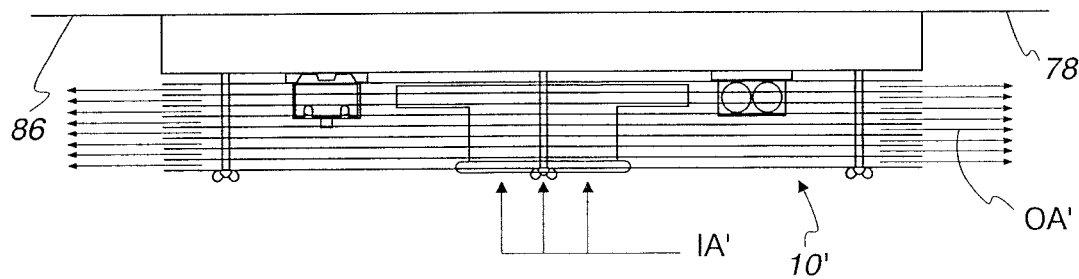
FIG. 10 is a view as in FIG. 9 with the air treatment unit in an operative state.

A like, or identical, unit 10' can be flush mounted to a surface 86, as shown in FIGS. 8-10. Mounting may be effected with the bottom wall 56' separated, as shown in FIG. 9, to facilitate access to a top wall 80 through the primary treatment volume 28'. This also facilitates the connection of the wires 82 within a junction box 88 on the wall 90 defining the mounting surface 86. Conventional fasteners 92 can be used to secure the flange 76 against the surface 86 to maintain the unit 10' in its operative position, as shown in FIG. 10. Air flow pattern is identical to that shown in FIG. 7, as indicated by the arrows IA', OA'.

In FIGS. 11-14, a modified form of air treatment unit is shown at 10", including sequence drawings showing how the same is installed with respect to ceiling T-bar components 40 on a drop ceiling.

The air treatment unit 10" is substantially the same as the air treatment unit 10', with the main difference being that the air moving assembly/fan 18" is mounted to depend from a downwardly facing surface 94 on the bottom wall 56".

Figure 11:
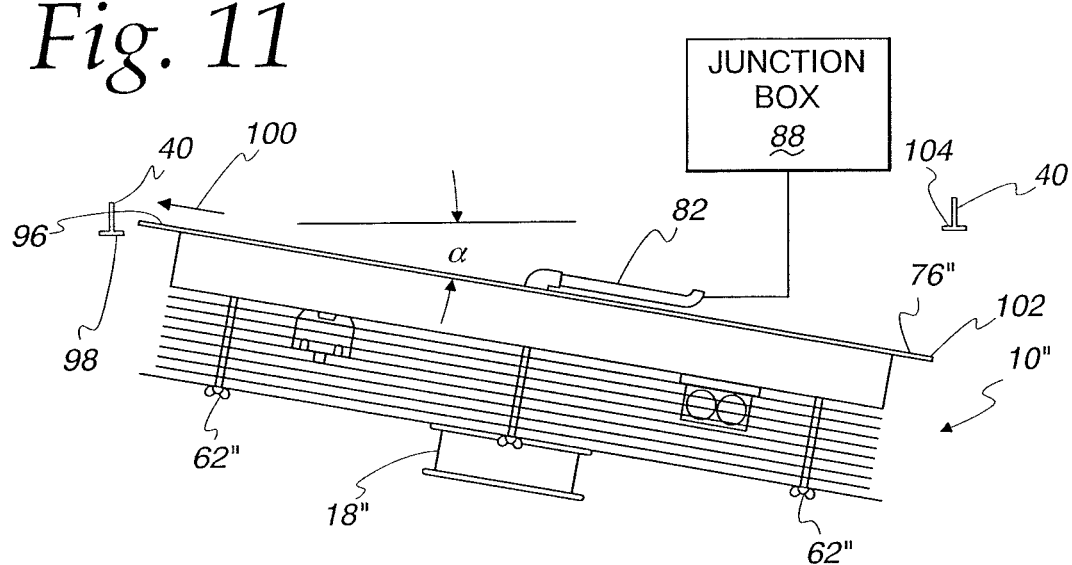
FIG. 11 is a side elevation view of a further modified form of air treatment unit, according to the invention, in a preassembly position with respect to T-bar components on a drop ceiling.
Figure 12:
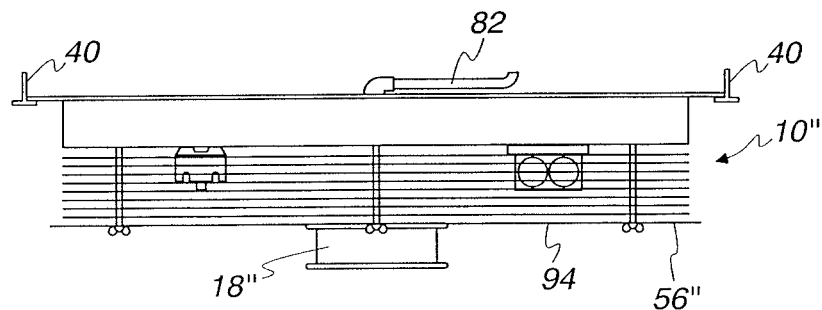
FIG. 12 is a view as in FIG. 11 with the air treatment unit in an operative state.
Figure 14:
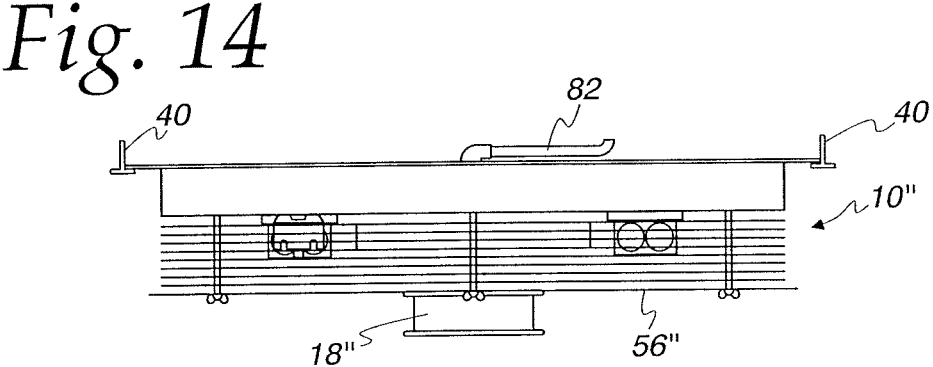
FIG. 14 is a view as in FIG. 13 with the wall reattached.

FIG. 11 also shows the initial step for placing the air treatment unit 10" in its operative position of FIG. 14. As shown, the entire air treatment unit is placed at an angle α to horizontal. In this orientation, a leading end 96 of the flange 76" is situated so that it can be directed over a horizontal leg 98 on the T-bar component 40. By then being shifted in the direction of the arrow 100, the trailing end 102 of the flange 76" can be tipped upwardly and will clear a leg 104 of the T-bar component 40 shown on the right side in FIG. 11. The entire air treatment unit 10" can then be shifted to the right in FIG. 11 so that the flange 76" bridges, and is supported cooperatively by, the legs 98, 104.

The wires 82 can be electrically connected at the junction box 88.

Figure 13:
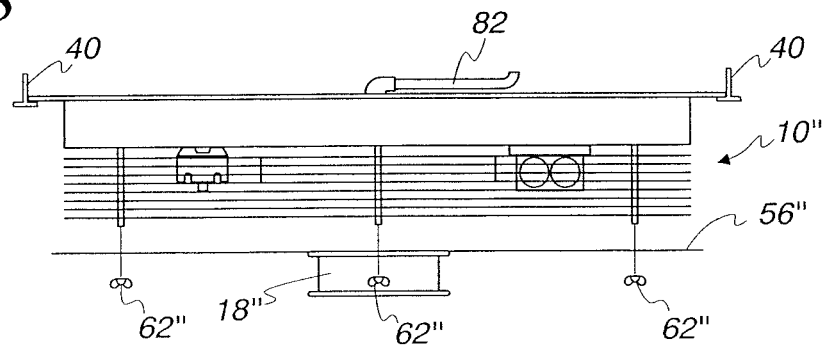
FIG. 13 is a view as in FIG. 12 with a bottom wall of the air treatment unit separated.

By separating the wingnuts 62", the bottom wall 56" and air moving assembly/fan 18" can be lowered as a unit, as shown in FIG. 13, to assist assembly, maintenance, cleaning, etc.

The bottom wall 56" can then be re-secured to assume the FIG. 14 state.

Figure 15:
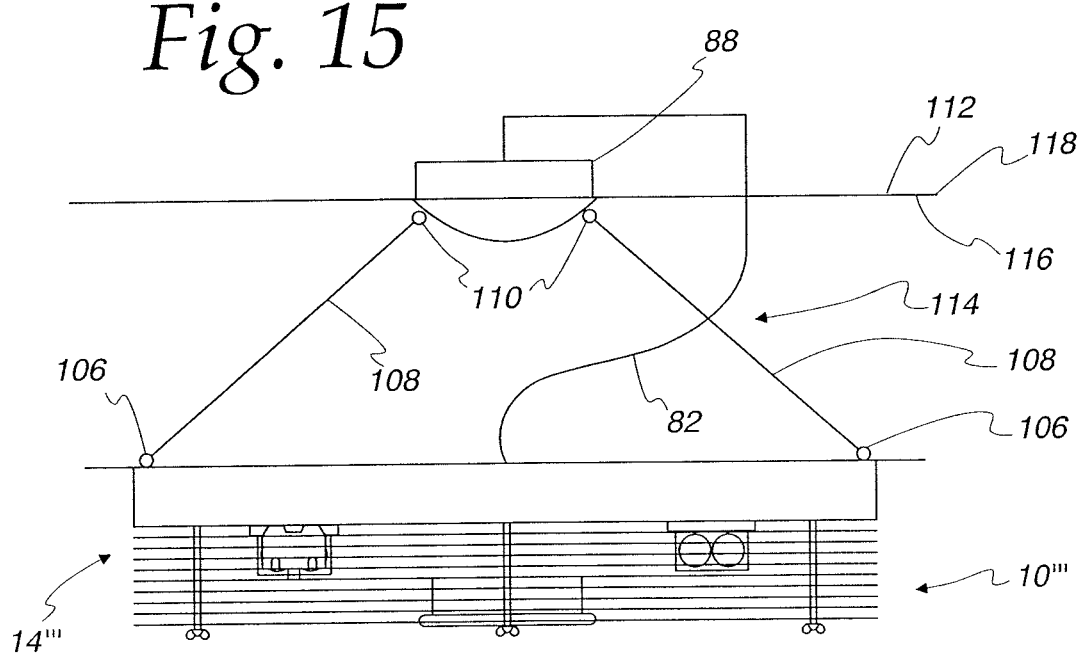
FIG. 15 is a side elevation view of a still further modified form of air treatment unit suspended in an operative state from a ceiling.

In FIG. 15, an air treatment unit is shown at 10''' that is substantially the same as the air treatment unit 10' with the exception that the frame 14'' has a plurality of mounting eyelets 106 fixed thereto. The eyelets 106 accommodate cables 108 which connect between the eyelets 106 and separate eyelets 110 fixed to a wall 112 at which the frame 14''' is operatively positioned. The eyelets 106, 110 and cables 108 cooperatively make up a suspension assembly at 114 through which the frame 14''' is spaced from a downwardly facing surface 116 on a wall 118 with the frame 14''' operatively positioned.

Of course, virtually any type of a conventional structure might be used to make up the suspension assembly to establish the relationship between the air treatment unit 10''' and the associated wall 118.

Wires 82 can be extended from the frame 14''' to the junction box 88 to electrically connect operating components.

With all embodiments, the main frame portions and subframe portions may be configured to define spaces for electrical components and wiring needed to power the lamps, air moving assemblies, etc. It is not necessary to get into all of the details of the electrical components and their connection, as one skilled in the art would be able to readily devise different component arrangements to achieve the objectives set forth herein.

As noted above, the inventive air treatment unit can be used to replace a supply vent conventionally used to distribute air in an occupied space. Alternatively, a more passive interaction between the air treatment unit and an existing duct outlet is effected.

The air treatment unit can be operated to disinfect with air movement induced through the duct 24 and/or by the air moving assembly 18. That is, the forced air source 26 and air moving assembly 18 may be separately operated or operated together, in the latter case causing a synergistic effect.

Many different variations of the above-described structure are contemplated. Several such variations are described hereinbelow using the same basic components and concepts described above, with it being understood that all like functioning components are interchangeable between the different embodiments.

In one form, the basic air treatment unit 10 may be made without its own, or any, air moving assembly, identified at 18 in FIGS. 1-3. With the dotted line showing of the air moving assembly 18 in FIGS. 1-3, the schematic representations depict the air treatment unit 10 in alternative forms both with and without an air moving assembly 18 being a part thereof.

In other words, the invention contemplates that air flow is somehow induced into the volume 20/primary treatment volume 28 and therefrom in a radial direction relative to a reference axis for the volume 20/preliminary treatment volume 28 to produce the radially outwardly moving air pattern that ultimately results in disinfected air being distributed into the space 22.

This air flow can be induced by an air moving assembly 18 that is part of the air treatment unit 10, an air moving assembly spaced from the frame 14 and dedicated to operation of the air treatment unit 10, or another structure, such as one causing air to be delivered through an outlet 200 on a duct 24, as shown in FIGS. 1 and 3, from the source 26 to condition the space 22, as by cooling, heating, moisturizing, dehumidifying, etc.

Alternatively, conditions in a room may cause natural convection which more passively causes the air to move guidingly into the volume 20/primary treatment volume 28, and in a radially outwardly moving pattern, during which movement the air is disinfected by the light rays from the UV light source 16.

Figure 16:
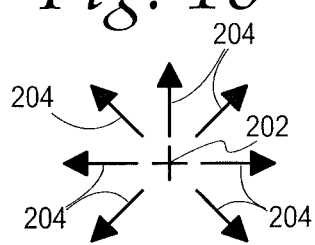
FIG. 16 is a schematic representation showing an axis for a primary treatment volume on the inventive air treatment unit and indicating an outwardly moving pattern of air from within the primary treatment volume.

In further explaining variations of the above embodiments, description is made with reference to an axis, generally identified at 202 in FIG. 16. The axis 202 extends through the volume 20/primary treatment volume 28 and generally represents the location away from which air flow is directed from within the volume 20/primary treatment volume 28 in a "radial" direction, as indicated by the arrows 204.

In the specific embodiments illustrated in FIGS. 4-15, and described hereinabove, the air travels in a radially outwardly moving pattern substantially fully around the reference axis, which corresponds to what is depicted schematically in FIG. 16. It should be understood that within the description of a full 360° pattern around a reference axis, it is contemplated that there might be certain frame structures or other structures that block some of the radial flow. However, even with such discrete blockage, the overall pattern is considered to be substantially a full 360°.

The basic concepts and structures described above can also be adapted to deliver disinfected air in a radial outward pattern that is dictated by the geometry of the region at which the air treatment unit 10 is placed. For example, a modified air treatment unit 10a might be placed at an inside corner location at 206. From the reference axis 202a, the angular dimension θa for the radially outwardly moving pattern of disinfected air, indicated by the arrows 204a, is on the order of 90°.

Another form of air treatment unit 10b may be matched to an outside corner region at 208 whereby the angle θb around the axis 202b, corresponding to the angle θa, is on the order of 270°. The arrows 204b show the direction of the radially outwardly moving air pattern.

Figure 19:
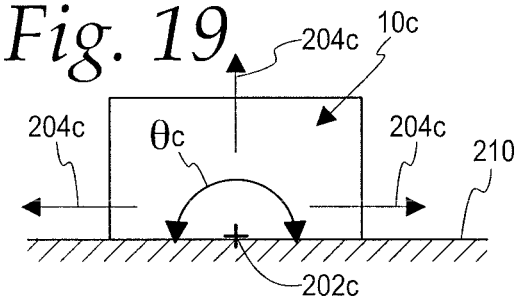
FIG. 19 is a view as in FIGS. 17 and 18 with the inventive air treatment unit adapted to operate at a straight vertical wall.

As shown in FIG. 19, an air treatment unit 10c may be placed against a vertical wall surface 210 whereby the flow pattern angle θc around the axis 202c, indicated by the arrows 204c, is on the order of 180°.

Figure 17:
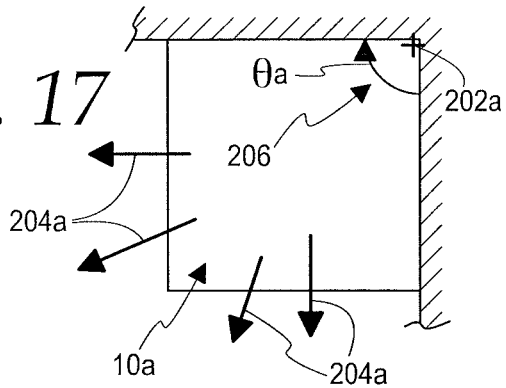
FIG. 17 is a view similar to that in FIG. 16 with the inventive air treatment unit adapted to operate at an inside corner location.
Figure 18:
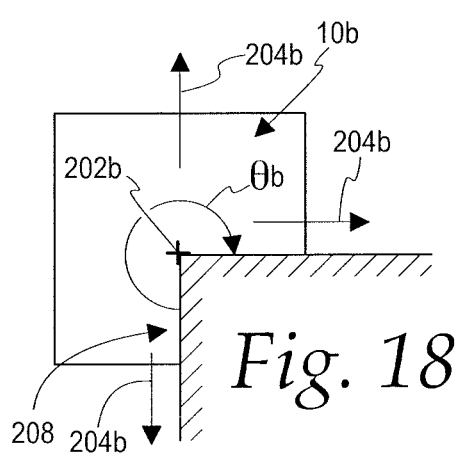
FIG. 18 is a view as in FIG. 17 with the inventive air treatment unit adapted to operate at an outside corner.

It should also be emphasized that heretofore, the axis 44, corresponding to the axis 202, has been generally designated as vertical, which is a preferred orientation for the air treatment unit, whether suspended from a ceiling or wall mounted. The arrangements shown in FIGS. 17-19 can be ceiling and/or wall mounted. However, the reference axis may be horizontal and at any angle between horizontal and vertical. In all embodiments, whether the axis identified generically or as "vertical", the intent herein throughout the Detailed Description and claims is that the axis orientation is not limited by its orientation, with "vertical" being adopted to provide a simple frame of reference throughout the description and claims.

Starting with the generic descriptions above, and using components in the exemplary embodiments, numerous different variations of the air treatment unit, with and without an air moving assembly, can be produced, representative ones of which are shown schematically in FIGS. 20-26, below.

Figure 20:
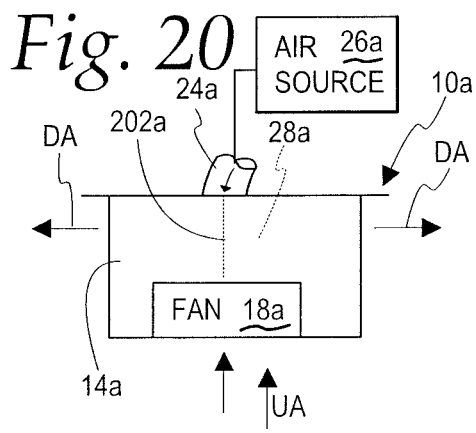

As shown in FIG. 20, the air moving assembly 10a effectively is a combination of: a) a fan 18a on a frame 14a, which fan 18a moves air parallel to the axis 202a' upwardly into the primary treatment volume 28a; and b) a forced air source 26a delivering air axially downwardly through a duct 24a that causes flow mixing, resulting in untreated air being drawn axially upwardly by the fan 18a and disinfected air being discharged radially from the primary treatment volume 28a as respectively indicated by the arrows DA (disinfected air flow) and UA (untreated air flow). As in the prior embodiments, UV rays may effect further air treatment radially outside the frame 14a, as potentially occurs with the other embodiments in FIGS. 21-30, described below.

Figure 21:
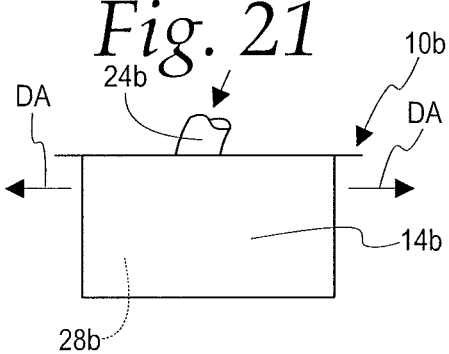

FIG. 21 discloses an air treatment unit 10b, with a frame 14b, similar to the air treatment unit 10a in FIG. 20, with an air inputting duct 24b but without any fan corresponding to the fan 18a. The direction of disinfected air is, as shown by the arrows DA, similar to that in FIG. 20, without the effects of turbulence resulting from the colliding air inputs. Provision may be made to circulate room air back into the primary treatment volume 28b.

Figure 22:
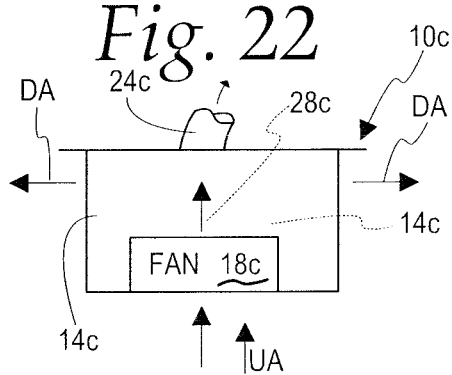

In FIG. 22, an air treatment unit 10c is depicted wherein a fan 18c on a frame 14c is incorporated as in FIG. 20 but with a duct 24c drawing air so as to cause it to move oppositely to how air moves in the duct 24a, thereby producing a low pressure region within the primary treatment volume 28c. The result of this construction is that untreated air flows axially inwardly as indicated by the arrows UA, with disinfected air flowing radially outwardly as indicated by the arrows DA.

Figure 23:
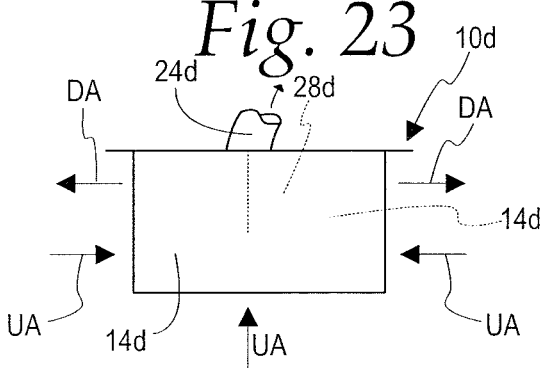

The air treatment unit 10d in FIG. 23 is similar to that in FIG. 22, but does not use a fan, corresponding to the fan 18c, on its frame 14d. Air flows in the duct 24d in the same direction as the air flows in the duct 24c in FIG. 22, thereby to produce a low pressure volume with a resulting radial and/or axial inflow to the primary treatment volume 28d of untreated air, as indicated by the arrows UA, and outflow of disinfected air, as indicated by the arrows DA.

In FIG. 24, an air treatment unit 10e corresponds to the unit 10a in FIG. 20, without any axial delivery of air through any duct corresponding to the duct 24a. A fan 18e, on a frame 14e, moves air axially into the primary treatment volume 28e, thereby causing radial delivery of disinfected air, as indicated by the arrows DA.

FIG. 25 depicts an air treatment unit 10f, corresponding in construction to the air treatment unit 10e, with the exception that a fan 18f on a frame 14f moves the air axially from the primary treatment volume 28f. This produces a low pressure at the lower region of the primary treatment volume 28f, thereby potentially allowing a certain volume of untreated air to be delivered radially to the primary treatment volume 28f from the space, as indicated by the arrows UA, and disinfected air to be expelled radially from the primary treatment volume 28f in the direction of the arrows indicated by DA.

FIG. 26 discloses an air treatment unit 10g with a frame 14g and which has no air moving assembly—fan or forced air—and thus relies upon natural convection to cause untreated air to migrate into the primary treatment volume 28g, with disinfected air discharged in the direction of the arrows DA.

The various configurations above are exemplary but do not make up all potential different layouts that might be devised, according to the invention, to cause different air movement to thereby induce flow of air into and from within the primary treatment volume in the radially outwardly moving pattern.

Further, in the FIG. 26 embodiment, the convection may be altered by other dedicated or non-dedicated structure(s). For example, temperature differences may cause air to move in paths that induce a flow of untreated air into the primary treatment volumes and expulsion of disinfected air therefrom. Natural flow of air caused by doors, vents, windows, etc. may facilitate this air flow pattern development.

As shown generically in FIG. 27, UV lamps 16a, 16b, 16c, 16d are preferably strategically placed in spaced relationship to the axis 202 in a surrounding arrangement whereby air is caused to be substantially uniformly exposed to UV rays generated by the lamps 16a-16d in operation. While four such lamps 16a-16d are shown, less than four or greater than four might be utilized depending upon the particular shape and size of the frame on the air treatment unit. Further, while straight UV lamp configurations are depicted above, the lamp shapes are not limited. For example, a curved shape might be integrated into the design, as could be a full ring-shaped lamp.

The UV lamps 16a-16d are selected to optimize air treatment. As noted above, there are different zones of treatment resulting from the basic design described above. That is, the air is preferably exposed within the primary treatment volume to a relatively uniform density of ultraviolet rays. Between the aforementioned slats, the louver volume is exposed to ultraviolet rays, which is identified above as the "kill zone". A more passive exposure of the air to the UV rays occurs as the air is expelled radially from the louver volume between slats. Thus, the overall system is designed to coordinate the exposure in these three zones to optimize the progressive disinfecting of the air, starting within the primary treatment volume and continuing to where the air resides outside of the frame and within the particular space in which treated air is desired.

FIG. 28 depicts a generic form of cooperating slats 212a, 212b, 212c, 212d, corresponding to the slats 46, described above. As depicted, each of the slats 212a-212d is of generally flat shape and resides effectively within a plane Pa, Pb, Pc, Pd, successively. Representative slats 212a, 212b have flat surfaces 214, 216, respectively, which face each other and bound a louver volume 218, making up a portion of the aforementioned "kill zone". The other slat pairs 212b, 212c; 212c, 212d cooperate in the same fashion. As depicted, the slats 212a-212d have the same shape and locations, as viewed from an axial perspective. While this is not required, a certain level of radial overlap, identified from the axial perspective, is preferred to create "kill" volumes in which air flow is effectively confined and guided. The planes thereof (Pa-Pd) are substantially orthogonal to the axis 202. There is no requirement that the slats have the same construction or that the spacing therebetween be identical. In the depicted form, the slats 212a-212d have the same configuration, spacing, and orientation.

While the frame perimeter from the axial perspective in the above-described embodiments is square or rectangular, this shape is not critical. For example, as shown in FIG. 29, the frame 14h could have a round shape, or any other shape best matched to its particular location, with an axis 202.

As further noted above, the ceiling mount is the most common location with a full 360° coverage. However, the same type of unit could be used on a vertical wall so that the axis 202 is horizontal, or assume another orientation, and still function effectively.

As depicted in the prior embodiments, multiple UV lamps are situated at substantially the same axial location. The lamps could be axially stacked or in a staggered relationship.

As depicted, the UV lamps are preferably at least partially radially inside of the slats 212 and the louver volumes 218 wherein air guidingly moving therethrough continues to be disinfected.

The invention is further directed to a method of treating air in a space, as shown in flow diagram form in FIG. 30.

As shown at block 220, an air treatment unit is obtained having a frame configured to define a primary treatment volume with an axis, together with a source of UV light.

As shown at block 222, the frame is placed in an operative position relative to a space in which air is to be treated.

As shown at block 224, air within the space is caused to be moved into the primary treatment volume and disinfected by being exposed to UV rays generated by the source of UV light and the disinfected air is controllably guided through the frame in a radially outwardly moving pattern extending through at least 90° around the axis.

Figure 31:
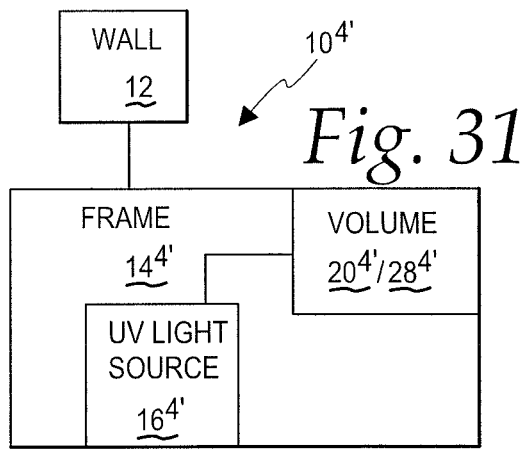
FIG. 31 is a schematic representation of another form of treatment unit, according to the present invention, having different selectable operating states.
Figure 32:
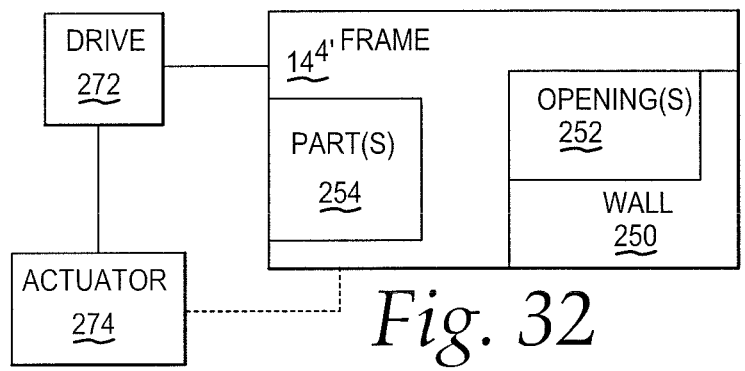
FIG. 32 is a schematic representation showing additional details of components on the treatment unit in FIG. 31, including one or more parts repositionable to change the state of the treatment unit.

Another generic form of treatment unit, according to the invention, is shown in FIGS. 31 and 32 at $10^{4'}$. The treatment unit $10^{4'}$ has a frame $14^{4'}$ with a volume $20^{4'}/28^{4'}$ within which air is treated by a UV light source $16^{4'}$ and caused to be dispersed away from the frame $14^{4'}$. The treatment unit $10^{4'}$ has different operating states, as described below.

The frame $14^{4'}$ is operatively mounted with respect to a wall 12 that may be a ceiling, vertical wall, etc.

The frame $14^{4'}$ has an associated wall 250 with at least one opening 252 therein to allow UV light rays to pass therethrough into a volume of space within which the air treatment unit resides with the treatment unit $10^{4'}$ in at least one of its operating states. The at least one opening 252 has an "effective area" through which the UV light rays pass to contact any surface within a space in direct line with the light generating portions of the UV light source $16^{4'}$ with the treatment unit $10^{4'}$ in at least one of its operating states.

At least one part 254 is provided that has different relationships with the at least one opening 252. In one relationship, the at least one part 254 is situated so that the at least one opening 252 has a first effective area, mentioned above. In a second relationship, the at least one part 254 at least partially blocks the at least one opening 252 so that the effective area thereof is less than the first effective area. The at least one part 254 may effectively fully block the at least one opening 252.

With this arrangement, the air treatment unit $10^{4'}$ is changeable between first and second states. In the first state, the at least one part 254 is situated relative to the at least one opening 252 whereby a predetermined part of the volume of space within which the air treatment unit resides is strategically blocked from direct exposure to UV light rays generated by the UV light source. In other words, at least part of the area defined by the at least one opening 252 is blocked so as not to allow passage thereinto of UV light rays from the UV light source $16^{4'}$.

In a second state, the relationship of the at least one part 254 to the at least one opening 252 is such that at least a portion of the aforementioned predetermined part of the volume of space within which the air treatment unit resides becomes directly exposed to UV light rays from the UV light source $16^{4'}$.

The change between the first and second states is characterized as changing the effective area of the at least one opening 252. The area is considered to be effectively changed even though the at least one part 254 may be simply blocking a certain pathway for UV light rays which will be considered herein as an effective reduction in area of the at least one opening 252.

As noted above, each of the volumes $20^{4'}$, $28^{4'}$ is considered to have an axis from which disinfected air distributes at least radially in a dispersion path. While the wall 250 in a preferred form is at a location where it blocks principally axial light ray transmission, this particular construction is not required. The wall 250 can be provided at any location with the at least one part 254 having a changed relationship with the at least one opening 252, as the treatment unit is changed between the first and second states, such that there is surface treatment over one area with the treatment unit in the second state and a reduction in area or blocking of the surface treatment in the first state.

By strategically constructing the treatment unit $10^{4'}$, including the construction and cooperation between the wall opening(s) 252 and associated part(s) 254, the treatment unit $10^{4'}$ can be changed selectively between states wherein it is used within a space primarily for surface treatment and one wherein it is used primarily to circulate disinfected air with controlled UV light ray projection, thereby to avoid direct contact with humans and animals within the space. The strategic construction of the components in FIG. 32, with many potential different configurations, potentially also affords the ability to simultaneously carry on both surface and circulating air treatment without potentially dangerous exposure of occupants of the space to UV light rays from the UV light source $16^{4'}$.

It should also be reemphasized that the description of orientation of axes, reference to top and bottom, etc., concerns relative terms which are not intended to be limiting. For example, the treatment unit $10^{4'}$ with substantially the same construction may be attached to a ceiling wall so that the axis of the primary treatment volume extends vertically or attached to a vertically extending wall so that the same axis extends substantially horizontally. In the latter case, the axially spaced regions are still considered to be top and bottom locations herein.

What is preferred with the construction in FIGS. 31 and 32 is that changing of state allows selection of primarily surface or air treatment or a combination thereof with controlling of direct exposure to UV light rays from the UV light source $16^{4'}$. The schematic showing of the treatment unit $10^{4'}$ is intended to encompass all basic structures described hereinabove, as well as those described below, with the ability to change between the first and second states.

Without limitation, the wall 250 may be any wall structure, whether or not described above. A modification of the bottom wall 54 will be used in examples, described below, but should not be viewed as limiting.

Figure 33:
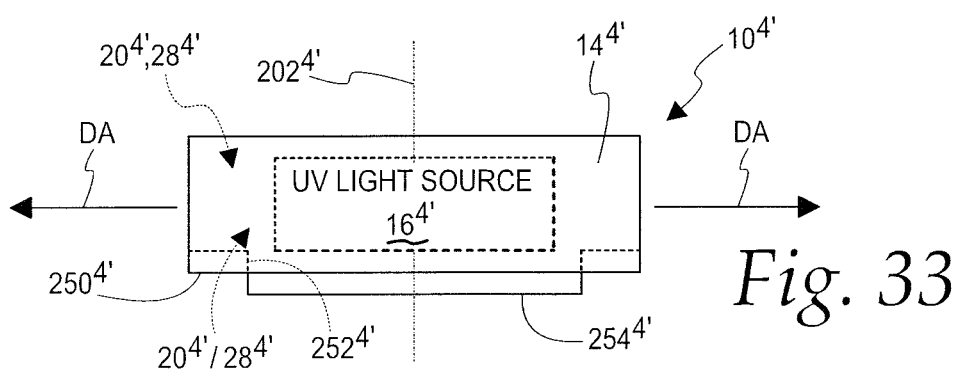
FIG. 33 is a side elevation view of one exemplary form of treatment unit as shown in FIGS. 31 and 32.
Figure 34:
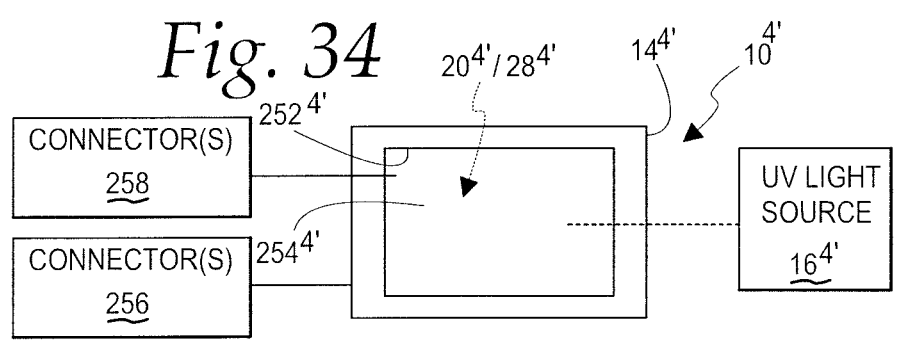
FIG. 34 is a bottom view of the treatment unit in FIG. 33.

In FIGS. 33 and 34, a treatment unit is shown at $10^{4'}$ with a frame $14^{4'}$ having a volume $20^{4'}/28^{4'}$ for air which is treated by a UV light source $16^{4'}$.

The volume $20^{4'}/28^{4'}$ has an axis $202^{4'}$, with disinfected air guided by the frame $14^{4'}$ generally radially outwardly in the direction of the arrow DA through a dispersion angle, preferably at least 90° and potentially through a full 360°.

The frame $14^{4'}$ has a bottom wall $250^{4'}$ with a substantially square opening $252^{4'}$ in communication with the volume $20^{4'}/28^{4'}$.

In this embodiment, the part $254^{4'}$ is releasably connectable to the frame $14^{4'}$, as shown in FIGS. 33 and 34, wherein the part $254^{4'}$ fully blocks the opening $252^{4'}$. In this configuration, the treatment unit $10^{4'}$ is in the first state as a result of which the treatment unit $10^{4'}$ serves primarily as a circulating air treatment unit.

At least one connector 256 is provided on the frame $14^{4'}$ that cooperates with at least one connector 258 on the part $254^{4'}$ to releasably maintain the part $254^{4'}$ in the connected relationship with the frame $14^{4'}$, as shown in FIGS. 33 and 34. The connectors 256, 258 may be capable of cooperating with or without the use of separate fasteners. Multiple different arrangements could be devised by one skilled in the art to allow releasable connection of the part $254^{4'}$.

Once the part $254^{4'}$ is repositioned/separated to expose the full area of the opening $252^{4'}$, the air treatment unit $10^{4'}$ is in the second state, whereupon the UV light rays from the UV light source $16^{4'}$ project in a diverging, generally conical volume axially downwardly from the frame $14^{4'}$.

As depicted, the volume of space blocked by the part $254^{4'}$ is directly below the air treatment unit $10^{4'}$. However, as noted above, this is not required.

While not specifically shown in FIGS. 31-34, it is intended that the air guidance assemblies, as described with respect to the embodiments above, as well as variations thereof, could be used with the treatment unit $10^{4'}$ as well as all additional embodiments described below.

Figure 35:
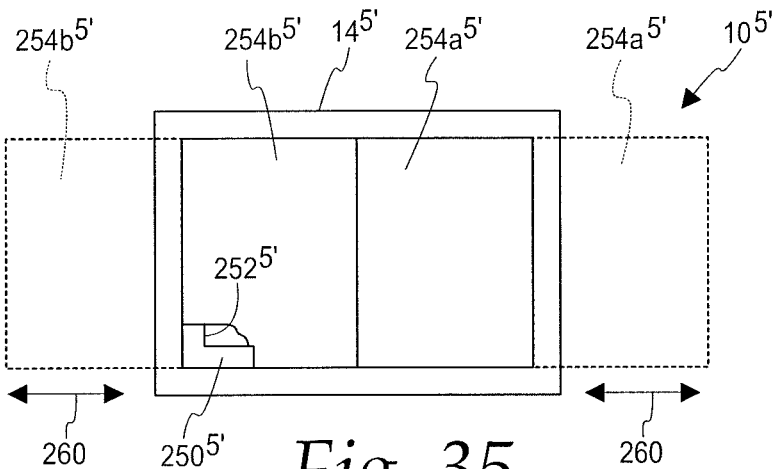
FIG. 35 is a view as in FIG. 34 of a modified form of treatment unit as shown in FIGS. 31 and 32.

In FIG. 35, a treatment unit is shown at $10^{5'}$ with a frame $14^{5'}$ generally corresponding to the frame $14^{4'}$.

In this embodiment, there are two parts $254a^{5'}$, $254b^{5'}$ that are translatable relative to the frame $14^{5'}$, between the solid line and dotted line positions for each, along lines as indicated by the double-headed arrows 260.

In the solid line positions, the parts $254a^{5'}$, $254b^{5'}$ cooperatively fully block the opening $252^{5'}$ in the wall $250^{5'}$.

With the parts 254a$^{5'}$, 254b$^{5'}$ in the solid line positions, the treatment unit 10$^{5'}$ is in the first state therefor, in this case fully blocking downward projection of UV light rays.

In the dotted line positions, the treatment unit 10$^{5'}$ is in the second state. In this case, the area at the opening 252$^{5'}$ is fully exposed for surface treatment.

The parts 254a$^{5'}$, 254b$^{5'}$ may be maintained in an intermediate position whereby the pattern of downwardly projecting UV light rays is changed.

Figure 36:
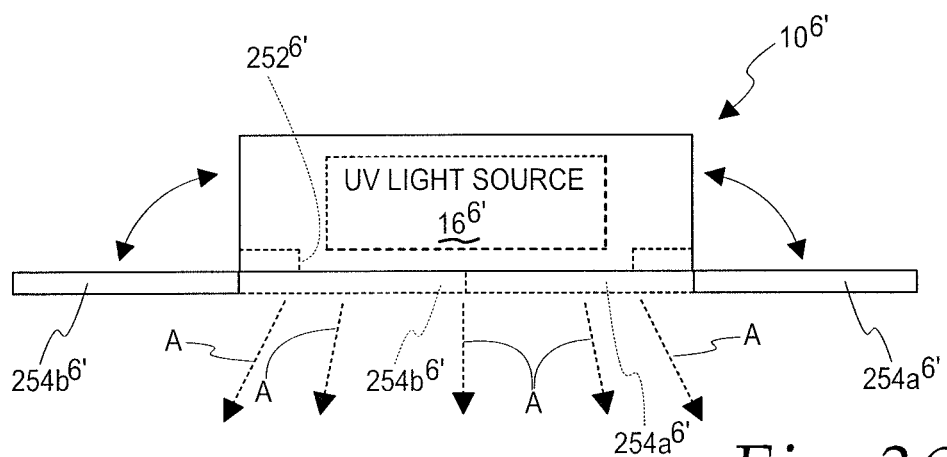
FIG. 36 is a side elevation view of another form of treatment unit as shown in FIGS. 31 and 32.

In FIG. 36, another form of treatment unit is shown at 10$^{6'}$ wherein the parts 254a$^{6'}$, 254b$^{6'}$ are pivotable relative to a frame 14$^{6'}$ between solid and broken line positions, with the latter representing the first state for the treatment unit 10$^{6'}$ and the latter representing the second state for the treatment unit 10$^{6'}$. In the second state, UV light rays from the UV light source 16$^{6'}$ project in a diverging volume, indicated by the arrows A from the wall opening 252$^{6'}$.

Figure 37:
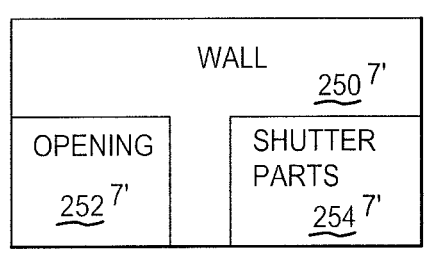
FIG. 37 is a schematic representation of another form of the parts, as shown schematically in FIG. 32, that are repositionable to change the state of the treatment unit.

FIG. 37 represents another variation of wall 250$^{7'}$ with an opening 252$^{7'}$ having an effective area that is variable as by using parts 254$^{7'}$ typical of those used on a camera shutter associated with a lens.

The above are just examples of specific forms contemplated within the generic showing in FIGS. 31 and 32. The generic showing is intended to encompass not only these versions but virtually an unlimited number of variations of the components and their interaction that would be obvious to one skilled in the art with the present teachings in hand.

Figure 38:
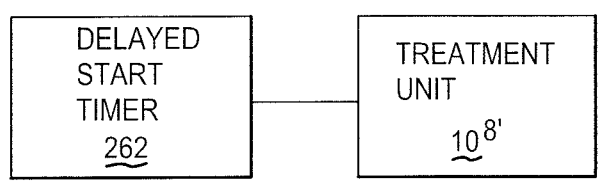
FIG. 38 is a schematic representation of another form of the inventive treatment unit with a delayed start timer.

As shown in FIG. 38, another form of treatment unit 10$^{8'}$ may incorporate a delayed start timer 262 which can be set to at least one of: a) cause the treatment 10$^{8'}$ to change from its "off" state into its "on" state; and b) cause the treatment unit to change between the first and second states, after a predetermined time interval. It is anticipated that the delayed start timer 262 might be incorporated into any of the embodiments hereinabove described.

Figure 39:
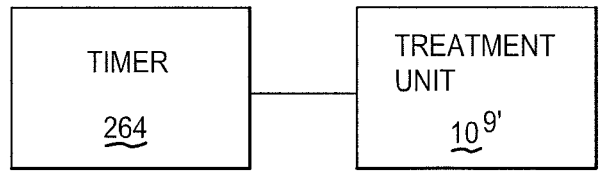
FIG. 39 is a schematic representation of another form of the inventive treatment unit with an operating timer.

In a further modification, a separate timer 264, as shown in FIG. 39, might be incorporated into the treatment unit 10$^{9'}$, intended to represent all treatment units herein, as well as others. The timer 264 is operable to cause the treatment unit 10$^{9'}$ to be one of: a) maintained in the "on" state; and b) operated in the second state, for a predetermined time interval.

Figure 40:
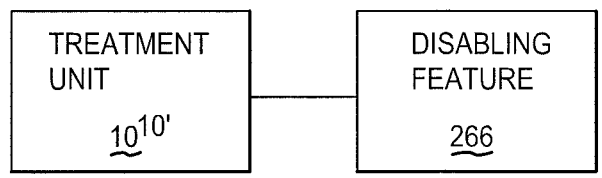
FIG. 40 is a schematic representation of another form of the inventive treatment unit with a disabling feature.

As shown in FIG. 40, in one form, a treatment unit 10$^{10'}$, representative of all treatment units herein, and others, has a disabling feature 266 that causes the treatment unit 10$^{10'}$ to be changed from one of: a) its "on" state into its "off" state; and b) its second state into its first state upon a predetermined triggering event occurring at a location spaced from the treatment unit.

Figure 41:
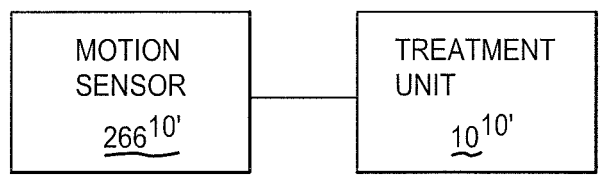
FIG. 41 is a schematic representation corresponding to FIG. 40 with the disabling feature specifically in the form of a motion sensor.

In one form, as shown in FIG. 41, the disabling feature 266$^{10'}$ incorporates a motion sensor, on or separate from the treatment unit 10$^{10'}$, that detects motion, in a space generally or in the vicinity of the treatment unit 10$^{10'}$. Thus, the system might be programmed so that with the treatment unit 10$^{10'}$ on and in the second state, a user's movement in the vicinity of the treatment unit 10$^{10'}$ may cause the treatment unit 10$^{10'}$ to be turned off, or its state changed, to protect a human or animal from being directly exposed to UV light rays.

Figure 42:
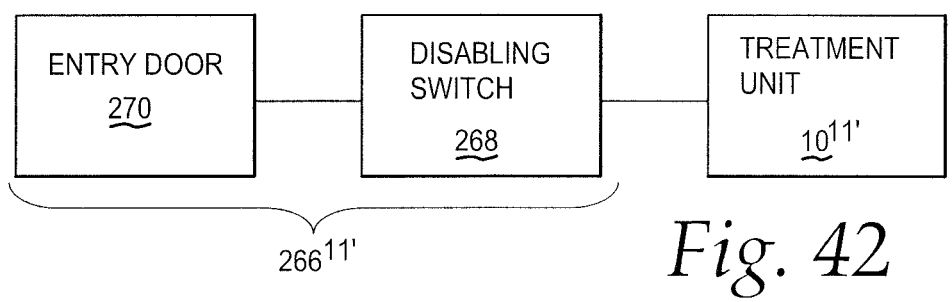
FIG. 42 is a schematic representation of another form of the inventive treatment unit with the disabling feature in the form of a disabling switch operated through repositioning of an entry door.

In an alternative form, as shown in FIG. 42, a treatment unit 10$^{11'}$ may have an associated disabling switch 268 that is operable by an entry door 270 movable between open and closed positions. The disabling switch 268 and entry door 270 define the disabling feature 266$^{11'}$.

By using an opening at which the entry door 270 is located to enter and leave a space within which the treatment unit 10$^{11'}$ is located, a changing of the entry door 270 from its closed position into its open position activates the disabling switch 268, thereby causing the treatment unit 10$^{11'}$ to be changed from one of: a) its "on" state into its "off" state; and b) its second state into its first state so as to thereby protect persons or animals within the space from being directly exposed to UV light rays generated by the treatment unit 10$^{11'}$.

In each embodiment, the repositionable part 254 may be manually moved as by direct engagement thereof. For example, one or more of the parts 254a$^{5'}$, 254b$^{5'}$ in FIG. 35 might be engaged and manually translated.

Alternatively, the part(s) 254 might be repositioned through an operable drive 272, as shown in FIG. 32. The drive 272 may be controlled by an actuator 274 that might be on the frame 14$^{4'}$ as indicated by dotted lines, or remotely situated therefrom. In the latter case, the actuator 274 might be operated from externally of a room to avoid inadvertent exposure of a user or animals to UV light. The actuator 274 may use any type of connection, such as Bluetooth, or otherwise.

Figure 43:
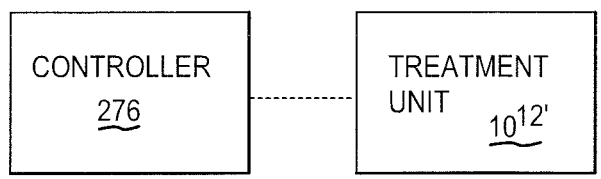
FIG. 43 is a schematic representation of a generic controller for operating features of the inventive treatment units.

It is contemplated that a controller 276, as shown in FIG. 43, remote from the treatment unit 10$^{12'}$, can be used to control all functions associated with the treatment unit 10$^{12'}$—notably, but not exclusively: a) turning the entire treatment unit off; b) turning off the UV light source; c) turning off a moving assembly; d) changing between first and second states; etc. The controller 276 could use a wired connection, and may be located internally or externally of a room in which the treatment unit 10$^{12'}$ is placed or may be a wireless controller 276, such as a smartphone, tablet, etc., using wireless, such as Bluetooth, technology.

The foregoing disclosure of specific embodiments is intended to be illustrative of the broad concepts comprehended by the invention.

The invention claimed is:

1. A method of treating a space, the method comprising the steps of:
    obtaining an air treatment unit comprising:
    a frame; and
    a source of UV light,
    the frame configured to define a primary treatment volume with an axis,
    the frame further comprising an air guidance assembly,
    the air treatment unit configured so that air within the primary treatment volume is guided by the frame to move radially outwardly from the primary treatment volume through a dispersion angle,
    air within the primary treatment volume exposed to UV light rays from the UV light source so that air that moves radially outwardly from the primary treatment volume is disinfected; and
    changing the air treatment between: a) a first state wherein a predetermined part of a volume of space outside of the air treatment unit and within which the air treatment unit resides is strategically blocked from direct exposure to UV light rays generated by the UV light source; and b) a second state wherein at least a portion of the predetermined part of the volume of space is directly exposed to UV light rays from the UV light source,
    wherein the air treatment unit has a top and a bottom spaced axially from the top,
    wherein with the air treatment unit in the second state at least part of the at least portion of the predetermined part of the volume of space that is directly exposed to UV light rays from the UV light source is below the air treatment unit.

2. The method of treating a space according to claim 1 wherein the dispersion angle is at least 90°.

3. The method of treating a space according to claim 1 wherein with the air treatment unit in the first state at least a portion of the predetermined part of the volume is directly below the air treatment unit.

4. The method of treating a space according to claim 1 wherein the frame has a wall with at least one opening with a first effective area through which UV light rays from the source of UV light are directed with the air treatment unit in the second state.

5. The method of treating a space according to claim 4 wherein with the air treatment unit in the first state, the at least one opening has an effective area less than the first effective area.

6. The method of treating a space according to claim 4 wherein the wall is a bottom wall and with the air treatment unit in the first state, the at least one opening is substantially fully blocked.

7. The method of treating a space according to claim 1 wherein the air treatment unit further includes an air moving assembly which induces movement of air radially outwardly from the primary treatment volume.

8. The method of treating a space according to claim 7 wherein the air moving assembly is maintained on the frame.

9. The method of treating a space according to claim 1 wherein the air treatment unit further includes an air moving assembly which induces movement of air from within a space in which the air treatment unit resides into the primary treatment volume.

10. The method of treating a space according to claim 1 wherein the air guidance assembly guides air within the primary treatment volume in movement radially outwardly from the primary treatment volume.

11. The method of treating a space according to claim 1 wherein the air guidance assembly is configured to define at least one elongate opening through which air within the primary treatment volume is communicated in moving radially outwardly from the primary treatment volume.

12. The method of treating a space according to claim 11 wherein the air guidance assembly comprises a plurality of spaced slats and the at least one elongate opening comprises a louver volume between at least first and second of the spaced slats.

13. The method of treating a space according to claim 12 wherein the first and second spaced slats are in radially overlapping relationship.

14. The method of treating a space according to claim 12 wherein the air treatment unit is configured to create multiple zones in which air is treated differently by UV light rays from the UV light source, wherein the multiple zones comprise: a) a first zone in the primary treatment volume; and b) a second zone in the louver volume.

15. The method of treating a space according to claim 14 wherein the multiple zones further comprise a third zone that is radially outside of the first and second slats.

16. The method of treating a space according to claim 12 wherein the first and second slats are substantially flat and reside in first and second planes that are substantially orthogonal to the axis of the primary treatment volume.

17. The method of treating a space according to claim 1 wherein the UV light source comprises a UV lamp residing one of: a) within; and b) adjacent to, the primary treatment volume.

18. The method of treating a space according to claim 1 wherein the air treatment unit further comprises delayed start timer and further including the step of setting the delayed start timer to thereby cause the air treatment unit to change between the first and second states, after a predetermined time interval.

19. The method of treating a space according to claim 18 wherein the air treatment unit has on and off states and a timer is operated to cause the air treatment unit to be one of: a) maintained in the on state; and b) operated in the second state, for a predetermined time interval.

20. The method of treating a space according to claim 1 wherein the air treatment unit comprises at least one blocking part that is repositioned to change the air treatment unit between the first and second states.

21. The method of treating a space according to claim 1 wherein the air treatment unit has an on state and an off state and further comprises a disabling feature that causes the air treatment unit to be changed from one of: a) the on state into the off state; and b) the second state into the first state upon a predetermined triggering event occurring at a location spaced from the air treatment unit.

22. The method of treating a space according to claim 21 wherein the air treatment unit is provided in a structure defining the space within which the air treatment unit is operatively placed, wherein the air treatment unit further comprises a motion sensor and the predetermined triggering event is movement of an object in the vicinity of the motion sensor.

23. The method of treating a space according to claim 22 wherein the structure has an entry door to the space within which the air treatment unit is operatively placed and movable between open and closed positions, the air treatment unit further comprises a disabling switch, and the predetermined triggering event is movement of the entry door from the closed position into the open position, whereupon the disabling switch causes the air treatment unit to be changed from the second state into the first state.

24. The method of treating a space according to claim 22 wherein the structure has an entry door to the space within which the air treatment unit is operatively placed and movable between open and closed positions, the air treatment unit further comprising a disabling switch, and the predetermined triggering event is movement of the entry door from the closed position into the open position, whereupon the disabling switch causes the unit to be changed from the on state into the off state.

25. The method of treating a space according to claim 1 wherein the air treatment unit has on and off states and further comprises a delayed start timer which is set to cause the air treatment unit to change from the off state into the on state after a predetermined time interval.

\* \* \* \* \*